United States Patent
Oki et al.

(10) Patent No.: US 10,849,486 B2
(45) Date of Patent: Dec. 1, 2020

(54) IMAGE ACQUISITION SYSTEM, IMAGE ACQUISITION METHOD, CONTROL DEVICE, AND CONTROL METHOD

(71) Applicant: Sony Corporation, Tokyo (JP)

(72) Inventors: Tomoyuki Oki, Kanagawa (JP); Akio Furukawa, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/609,745

(22) PCT Filed: Mar. 14, 2018

(86) PCT No.: PCT/JP2018/009839
§ 371 (c)(1),
(2) Date: Oct. 31, 2019

(87) PCT Pub. No.: WO2018/207456
PCT Pub. Date: Nov. 15, 2018

(65) Prior Publication Data
US 2020/0069164 A1    Mar. 5, 2020

(30) Foreign Application Priority Data
May 8, 2017  (JP) .................................. 2017-092443

(51) Int. Cl.
*A61B 1/06* (2006.01)
*G06T 7/00* (2017.01)
*H04N 5/225* (2006.01)

(52) U.S. Cl.
CPC .......... *A61B 1/0638* (2013.01); *G06T 7/0002* (2013.01); *H04N 5/2254* (2013.01);
(Continued)

(58) Field of Classification Search
CPC .. A61B 1/0638; G06T 7/0002; H04N 5/2254; H04N 5/2256
See application file for complete search history.

(56) References Cited

U.S. PATENT DOCUMENTS

| 6,359,724 B1* | 3/2002 | Katagiri ............... H01S 5/50 359/333 |
| 2003/0001951 A1* | 1/2003 | Tsujita ............... H04N 5/361 348/65 |

(Continued)

FOREIGN PATENT DOCUMENTS

| JP | 5-228098 A | 9/1993 |
| JP | 2003-290125 A | 10/2003 |

(Continued)

OTHER PUBLICATIONS

Extended European Search Report dated Feb. 28, 2020, issued in corresponding European Patent Application No. 18798270.7.

(Continued)

*Primary Examiner* — Mishawn N. Hunter
(74) *Attorney, Agent, or Firm* — Xsensus, LLP

(57) ABSTRACT

It is enabled to more appropriately prevent thermal damage to an area irradiated with illumination light.

An image acquisition system is provided including: a first light source unit that emits narrow band light having a peak intensity in a specific band; a second light source unit that emits wide band light having a band wider than the specific band; a generation unit that generates multiplexed light by using the narrow band light and the wide band light; an imaging unit that images an irradiation target of the multiplexed light; a prediction unit that performs prediction of a temperature of an area irradiated with the multiplexed light in the irradiation target; and a control unit that performs control of outputs of the narrow band light and the wide band light on the basis of the prediction.

20 Claims, 8 Drawing Sheets

(52) U.S. Cl.
CPC . *H04N 5/2256* (2013.01); *G06T 2207/10048* (2013.01); *G06T 2207/10056* (2013.01)

(56) References Cited

U.S. PATENT DOCUMENTS

| | | | |
|---|---|---|---|
| 2014/0273051 A1* | 9/2014 | Reddy | G01N 21/78 435/25 |
| 2015/0335385 A1 | 11/2015 | Miao et al. | |
| 2017/0343792 A1* | 11/2017 | Matsunobu | G02B 19/0047 |

FOREIGN PATENT DOCUMENTS

| | | |
|---|---|---|
| JP | 2011-200347 A | 10/2011 |
| JP | 2016-049370 A | 4/2016 |
| JP | 2016-120105 A | 7/2016 |
| WO | 2016/056459 A1 | 4/2016 |
| WO | 2016/092958 A1 | 6/2016 |
| WO | 2016/203985 A1 | 12/2016 |

OTHER PUBLICATIONS

International Search Report and Written Opinion dated Jun. 19, 2018 for PCT/JP2018/009839 filed on Mar. 14, 2018, 11 pages including English Translation of the International Search Report.

* cited by examiner

IMAGE ACQUISITION SYSTEM, IMAGE ACQUISITION METHOD, CONTROL DEVICE, AND CONTROL METHOD

CROSS-REFERENCE TO RELATED APPLICATIONS

The present application is based on PCT filing PCT/JP2018/009839, filed Mar. 14, 2018, which claims priority to JP 2017-092443, filed May 8, 2017, the entire contents of each are incorporated herein by reference.

TECHNICAL FIELD

The present disclosure relates to an image acquisition system, an image acquisition method, a control device, and a control method.

BACKGROUND ART

In recent years, researches for using multiplexed light generated by a plurality of types of light for various applications have been actively conducted. For example, in Patent Document 1 below, a technology is disclosed that uses multiplexed light generated by narrow band light and wide band light as illumination light, and images a specific biological structure with high contrast by changing a light amount ratio between the narrow band light and the wide band light.

CITATION LIST

Patent Document

Patent Document 1: Japanese Patent Application Laid-Open No. 2016-49370

SUMMARY OF THE INVENTION

Problems to be Solved by the Invention

However, the technology disclosed in Patent Document 1 has not been able to appropriately prevent thermal damage to an area irradiated with the illumination light. More specifically, the wide band light includes light of wavelength band components other than visible light, and an irradiation area may be damaged due to that the light of these wavelength band components is absorbed in the irradiation area (for example, a body part observed with an endoscope or the like), or the like.

The present disclosure has therefore been made in view of the above problem, and an object of the present disclosure is to provide a novel and improved image acquisition system, image acquisition method, control device, and control method enabled to more appropriately prevent the thermal damage to the area irradiated with the illumination light.

Solutions to Problems

According to the present disclosure, an image acquisition system is provided including: a first light source unit that emits narrow band light having a peak intensity in a specific band; a second light source unit that emits wide band light having a band wider than the specific band; a generation unit that generates multiplexed light by using the narrow band light and the wide band light; an imaging unit that images an irradiation target of the multiplexed light; a prediction unit that performs prediction of a temperature of an area irradiated with the multiplexed light in the irradiation target; and a control unit that performs control of outputs of the narrow band light and the wide band light on the basis of the prediction.

Furthermore, according to the present disclosure, an image acquisition method executed by a computer is provided, the image acquisition method including: emitting narrow band light having a peak intensity in a specific band; emitting wide band light having a band wider than the specific band; generating multiplexed light by using the narrow band light and the wide band light; imaging an irradiation target of the multiplexed light; performing prediction of a temperature of an area irradiated with the multiplexed light in the irradiation target; and performing control of outputs of the narrow band light and the wide band light on the basis of the prediction.

Furthermore, according to the present disclosure, a control device is provided including: a control unit that performs control of outputs of narrow band light and wide band light on the basis of prediction of a temperature of an irradiation area of multiplexed light generated by using the narrow band light having a peak intensity in a specific band and the wide band light having a band wider than the specific band.

Furthermore, according to the present disclosure, a control method executed by a computer is provided, the control method including: performing control of outputs of narrow band light and wide band light on the basis of prediction of a temperature of an irradiation area of multiplexed light generated by using the narrow band light having a peak intensity in a specific band and the wide band light having a band wider than the specific band.

Effects of the Invention

As described above, according to the present disclosure, it is enabled to more appropriately prevent the thermal damage to the area irradiated with the illumination light.

Note that, the above-described effect is not necessarily limited, and, in addition to the above-described effect, or in place of the above-described effect, any of effects described in the present specification, or other effects that can be grasped from the present specification may be exhibited.

MODE FOR CARRYING OUT THE INVENTION

Figure 1:
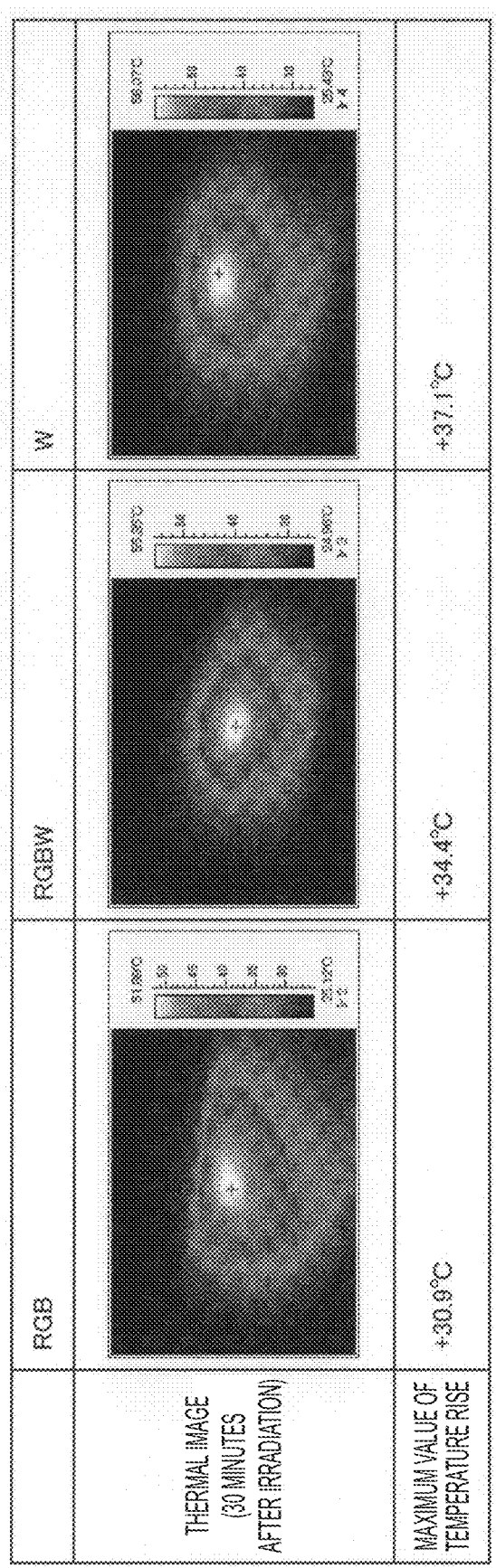
FIG. 1 is a diagram illustrating an experimental result representing that temperature rise in an irradiation area can be suppressed by control of outputs of narrow band light and wide band light.

Preferred embodiments of the present disclosure will be described in detail below with reference to the accompanying drawings. Note that, in the present specification and the drawings, constituents having substantially the same functional configuration are denoted by the same reference signs, and redundant explanations will be omitted.

Note that, the description will be made in the following order.

1. Background
2. Image Acquisition System According to the Present Embodiment
3. Image Acquisition System According to Modification
4. Hardware Configuration
5. Conclusion

1. Background

Various devices, methods, or systems have been variously studied that observe various objects by irradiating the objects with illumination light. For example, endoscopes are widely used as devices that observe internal structures of objects, such as a human body and a structure, by irradiating the inside of these objects with the illumination light. In the medical field, in particular, the endoscopes have been rapidly developed along with development of technologies regarding surgery and the like, and are now indispensable devices in many medical fields.

Here, in the endoscopes, regardless of a flexible scope or a rigid scope, as a light source for illumination, a light source may be used that emits light whose light spectrum is continuous and that has a band wider than a specific band (hereinafter, referred to as "wide band light" for convenience), such as a lamp light source (for example, a xenon lamp, a halogen lamp, or the like), or a white light emitting diode (LED) or the like. As one of features of the lamp light source, or the white LED or the like, it can be mentioned that the wide band light emitted from them includes light in a wavelength band other than a visible light band (for example, about 400 [nm] to about 700 [nm]).

Since the light in the wavelength band other than the visible light band is light that is invisible to an observer, the light is unnecessary for observation of an object. Furthermore, in a case where the light in the wavelength band other than the visible light band is absorbed by an observation object, energy of the absorbed light is converted to heat, so that the temperature of an area irradiated with the light in the observation object rises, and damage by the heat (hereinafter referred to as "thermal damage" for convenience. In particular, damage in the human body is referred to as "burn injury") may occur.

As for a general endoscope, it is clearly stated as a precaution that the thermal damage will occur in an observation area if the emission port of the illumination light is brought close to the observation object in a state where the illumination light is emitted with an output of a considerable degree. Therefore, for example, in surgery or the like, a surgeon prevents the burn injury from occurring by: avoiding performing close observation of an affected part for a long time using the endoscope and suspending the close observation as appropriate; performing surgery not requiring close observation; decreasing the output of the illumination light and increasing the gain of the imaging device; or the like. However, the surgery time is extended by the countermeasure such as suspending close observation, and noise of an obtained captured image is increased by the countermeasure to decrease the output of the illumination light and increase the gain of the imaging device.

Furthermore, for example, a technology has been developed that individually generates light having a peak intensity in a specific band (hereinafter referred to as "narrow band light" for convenience) such as red light, green light, or blue light, generates white light by multiplexing these types of the narrow band light, and uses the white light as the illumination light. Since the white light generated by the technology basically does not include the light in the wavelength band other than the visible light band (or light is weak in the wavelength band other than the visible light band), temperature rise can be suppressed in an irradiation area. However, since the narrow band light has a discrete light spectrum, the white light generated by multiplexing the multiple types of the narrow band light has a feature of low color rendering property.

The present discloser has therefore developed the present technology in view of the above circumstances. An image acquisition system, an image acquisition method, a control device, and a control method according to the present disclosure are able to prevent occurrence of the thermal damage by predicting a temperature of an area irradiated with multiplexed light generated by the narrow band light and the wide band light, and controlling outputs of the narrow band light and the wide band light on the basis of the prediction. Hereinafter, the technology according to the present disclosure will be described in detail in the order of "2. Image acquisition system according to the present embodiment", "3. Image acquisition system according to modification", and "4. Hardware configuration".

2. Image Acquisition System According to the Present Embodiment

First, an image acquisition system according to an embodiment of the present disclosure will be described. The present disclosure is applicable to various systems, devices, or methods. For example, the present disclosure is applicable to an image acquisition system that uses the illumination light in imaging processing, an illumination device (flashlight, stage lighting, or the like) that emits the illumination light, and the like (not limited to the exemplified system and device). In this document, a case will be described where the present disclosure is applied to an image acquisition system, as an example.

A type of the image acquisition system according to the present embodiment is arbitrary. For example, the image acquisition system according to the present embodiment may be a medical (or industrial) endoscope system, a medical (or industrial) microscope system, a security (or surveillance) camera system, or the like (not limited to the exemplified system). In this document, a case will be described where the image acquisition system according to the present embodiment is a medical endoscope system, as an example.

(2-1. Functional Outline of Image Acquisition System According to the Present Embodiment)

First, a functional outline will be described of the image acquisition system according to the present embodiment.

The image acquisition system according to the present embodiment multiplexes the narrow band light and the wide band light to generate white light, and uses the white light as the illumination light in the imaging processing. More specifically, the image acquisition system includes three types of narrow band light sources and one type of wide band light source, and the three types of narrow band light sources respectively emit red light, green light, and blue light, and the one type of wide band light source emits white light. Then, the image acquisition system generates white light to be used as the illumination light at the time of imaging by multiplexing the red light, green light, and blue light each being the narrow band light, and the white light being the wide band light by using a predetermined multiplexing optical system. Note that, a combination of wavelength bands of multiple types of light emitted from the respective narrow band light sources is arbitrary. For example, each narrow band light source may emit light of any wavelength band as long as white light is generated by multiplexing of multiple types of the narrow band light emitted from the respective narrow band light sources.

Then, the image acquisition system according to the present embodiment predicts a temperature of an area irradiated with the generated white light as the illumination light by a predetermined method. The prediction method is arbitrary. For example, the image acquisition system may predict the temperature of the irradiation area on the basis of the amount of light of reflected light or scattered light, which is incident on an imaging element, from the irradiation area, may determine a state of the irradiation area by analyzing a captured image and predict the temperature of the irradiation area on the basis of the determination result, or may predict the temperature of the irradiation area by using a device (for example, thermography or the like) that measures and visualizes heat of the irradiation area.

Moreover, the image acquisition system according to the present embodiment controls the outputs of the narrow band light and the wide band light on the basis of the prediction of the temperature of the irradiation area of the illumination light. More specifically, in a case where it is predicted that the temperature of the irradiation area is higher than a predetermined value (in other words, in a case where it is determined that the thermal damage may occur), the image acquisition system decreases the output of the wide band light, and increases the output of the narrow band light. As a result, in the multiplexed light, light in the wavelength band other than the visible light band included in the wide band light is decreased, so that the image acquisition system can suppress the temperature rise in the irradiation area due to absorption of the light.

Here, with reference to FIG. 1, an experimental result will be described representing that the temperature rise in the irradiation area can be suppressed by the control of the outputs of the narrow band light and the wide band light. FIG. 1 is a diagram illustrating an experimental result representing that the temperature rise in the irradiation area can be suppressed by the control of the outputs of the narrow band light and the wide band light. FIG. 1 illustrates the maximum value of the temperature rise in the irradiation area after a predetermined time has elapsed after the illumination light is emitted to a pig liver with the same output in each of: a case where multiplexed light of only the multiple types of the narrow band light (red light, green light, blue light) is used as the illumination light (indicated as "RGB" in FIG. 1); a case where multiplexed light of the multiple types of the narrow band light (red light, green light, blue light) and the wide band light (white light) is used as the illumination light (indicated as "RGBW" in FIG. 1. Note that the ratios are adjusted to be equal to each other between the amount of light of the narrow band light and the amount of light of the wide band light in the multiplexed light); and a case where only the wide band light is used as the illumination light (indicated as "W" in FIG. 1).

As illustrated in FIG. 1, the maximum values of the temperature rise of the irradiation area in respective cases are: 30.9 [° C.] in the case where the multiplexed light of only the multiple types of the narrow band light is used as the illumination light; 34.4 [° C.] in the case where the multiplexed light of the multiple types of the narrow band light and the wide band light is used as the illumination light; and 37.1 [° C.] in the case where only the wide band light is used as the illumination light. Also from the experimental results, it can be seen that the temperature rise in the irradiation area is suppressed by increasing the ratio of the narrow band light in the multiplexed light.

Conversely, in a case where it is predicted that the temperature of the irradiation area is lower than the predetermined value, the image acquisition system increases the output of the wide band light and decreases the output of the narrow band light as appropriate. As a result, the image acquisition system can improve color rendering property by increasing the ratio of the wide band light in the multiplexed light.

Furthermore, the image acquisition system according to the present embodiment can cause the output (brightness) and the color of the illumination light to be kept from changing (or cause the amount of change in each of the output (brightness) and the color to be maintained at a value within a predetermined range) before and after the above control. More specifically, the image acquisition system causes a total value of the amounts of light of the output of the narrow band light and the wide band light to be maintained at a constant value (or a value within a predetermined range from the constant value) before and after the above control. Furthermore, the image acquisition system causes the color temperature of the illumination light to be maintained at a constant value (or a value within a predetermined range from the constant value) before and after the above control. By these types of processing, the image acquisition system can cause the output (brightness) and the color of the illumination light to be constant before and after the above control. In other words, the image acquisition system does not have to perform control such as decreasing the amount of light of the illumination light and increasing the gain of the imaging element before and after the above control, and a captured image with low noise and easy observation can be provided to the observer. Details of the above processing will be described later.

(2-2. Configuration of Image Acquisition System According to the Present Embodiment)

The functional outline of the image acquisition system according to the present embodiment has been described above. Subsequently, a configuration will be described of the image acquisition system according to the present embodiment. The image acquisition system according to the present embodiment includes an image acquisition device 100 and a light source unit 200.

(Light Source Unit 200)

Figure 2:
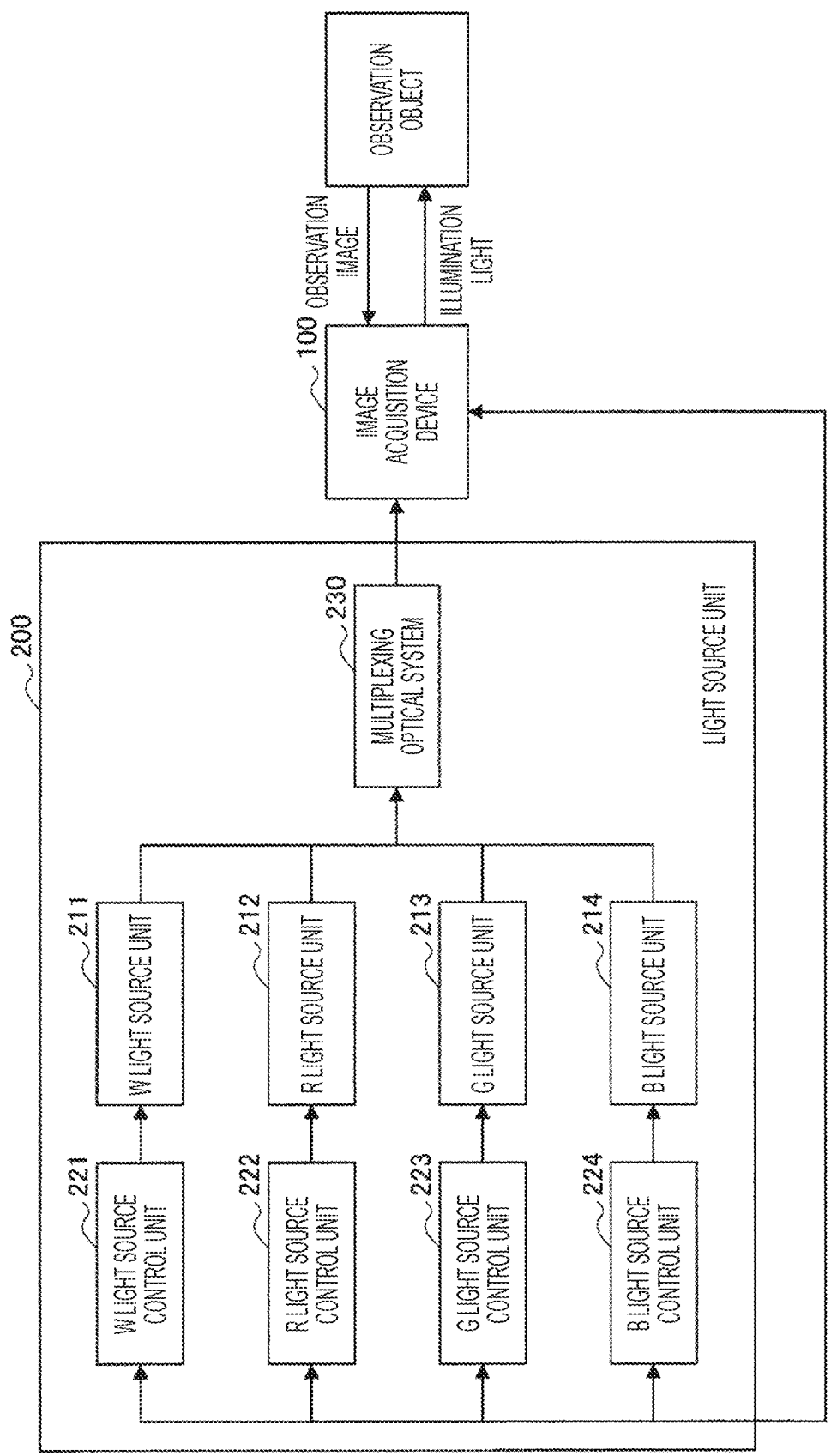
FIG. 2 is a block diagram illustrating an example of a configuration of a light source unit according to the present embodiment.

First, with reference to FIG. 2, a configuration will be described of the light source unit 200 according to the present embodiment. FIG. 2 is a block diagram illustrating an example of the configuration of the light source unit 200 according to the present embodiment. As illustrated in FIG. 2, the light source unit 200 according to the present embodiment includes a W light source unit 211, an R light source unit 212, a G light source unit 213, a B light source unit 214, a W light source control unit 221, an R light source control unit 222, a G light source control unit 223, a B light source control unit 224, and a multiplexing optical system 230.

(W light source unit 211, R light source unit 212, G light source unit 213, B light source unit 214)

The W light source unit 211, the R light source unit 212, the G light source unit 213, and the B light source unit 214 (hereinafter, these light source units may be collectively referred to as "each-color light source unit 210" for convenience) each are a light source that emits light of a predetermined wavelength band. More specifically, each of the R light source unit 212, the G light source unit 213, and the B light source unit 214 is configured to function as a first light source unit that emits narrow band light having a peak intensity in a specific band, and the R light source unit 212 emits red light, the G light source unit 213 emits green light, and the B light source unit 214 emits blue light. Furthermore, the W light source unit 211 is configured to function as a second light source unit that emits white light that is wide band light.

As the each-color light source unit 210, it is possible to use any of known laser light sources such as a semiconductor laser light source, a solid laser light source, a liquid laser light source, and a gas laser light source, a known LED, or the like depending on the wavelength band of light to be emitted. For example, by using any of various semiconductor laser light sources, further downsizing of the device can be achieved. Such a semiconductor laser light source is not particularly limited, but in this document, description will be made assuming that, as an example, a GaInP quantum well structure laser diode using a GaInP semiconductor is used as the R light source unit 212, and a GaInN quantum well structure laser diode using a GaInN semiconductor is used as each of the G light source unit 213 and the B light source unit 214. Furthermore, the description will be made assuming that a member that emits white light by causing a phosphor to emit light with a blue LED is used as the W light source unit 211. More specifically, the description will be made assuming that the member is used that uses a blue LED and a phosphor that is excited by blue light emitted by the blue LED and emits yellow light, and generates white light by multiplexing the emitted blue light and yellow light.

(W light source control unit 221, R light source control unit 222, G light source control unit 223, B light source control unit 224)

The W light source control unit 221, the R light source control unit 222, the G light source control unit 223, and the B light source control unit 224 (hereinafter, these light source units may be collectively referred to as "each-color light source control unit 220" for convenience) each control the each-color light source unit 210. More specifically, the each-color light source control unit 220 controls the each-color light source unit 210 by determining the output of light to be emitted from the each-color light source unit 210 and the timing of emitting the light, and the like, generating a control signal, and providing the control signal to the each-color light source unit 210. Furthermore, in a case where a control signal is provided from a control unit 110 of the image acquisition device 100 as described later, the each-color light source control unit 220 controls the each-color light source unit 210 on the basis of the control signal provided. For example, in a case where the control unit 110 of the image acquisition device 100 determines the output of light to be emitted from the each-color light source unit 210 and the timing of emitting the light, and the like, and provides a control signal including information regarding the output and the timing to the each-color light source control unit 220, the each-color light source control unit 220 controls the each-color light source unit 210 on the basis of the control signal provided.

(Multiplexing Optical System 230)

Figure 3:
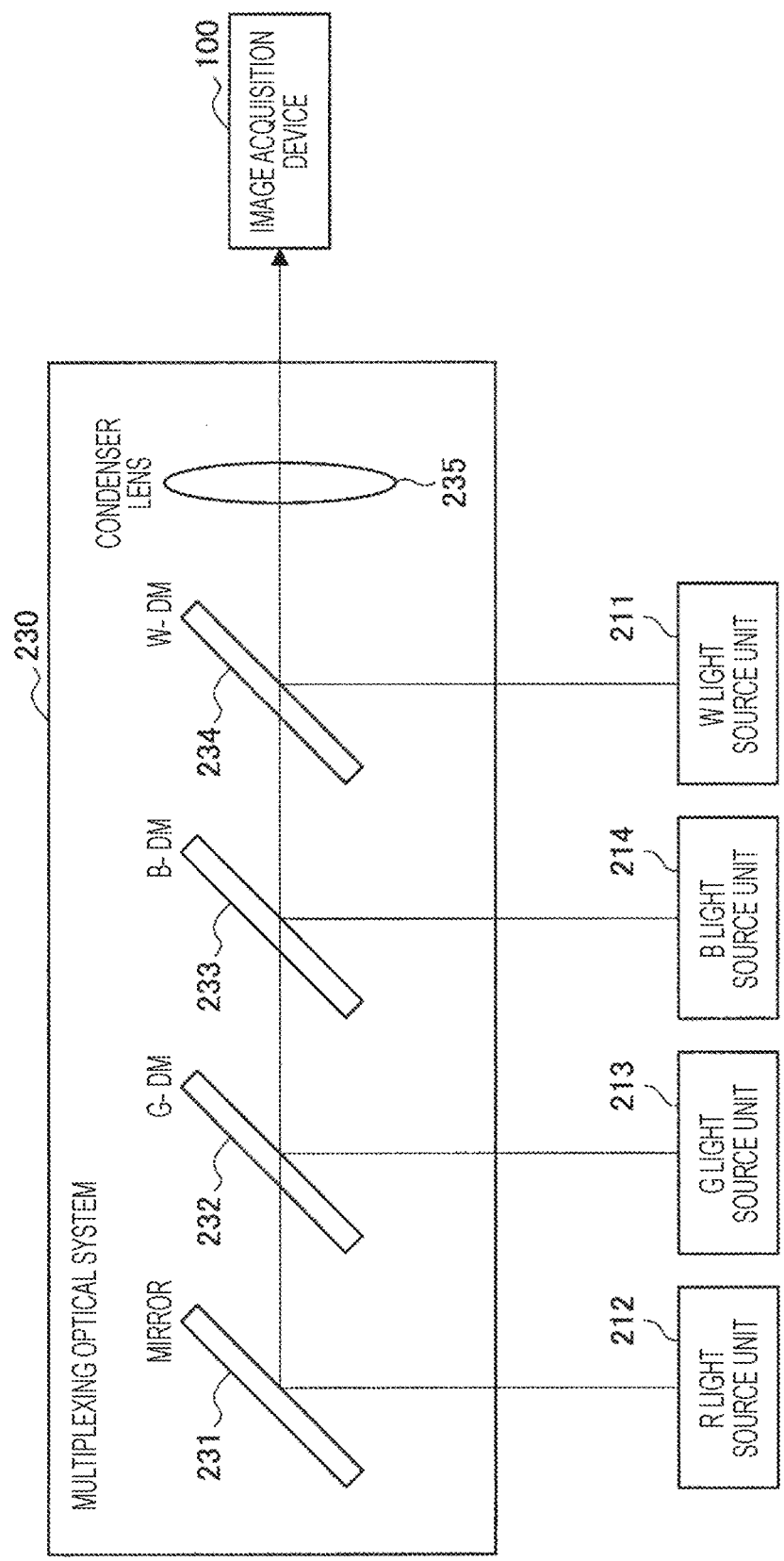
FIG. 3 is a block diagram illustrating an example of a configuration of a multiplexing optical system according to the present embodiment.
Figure 4:
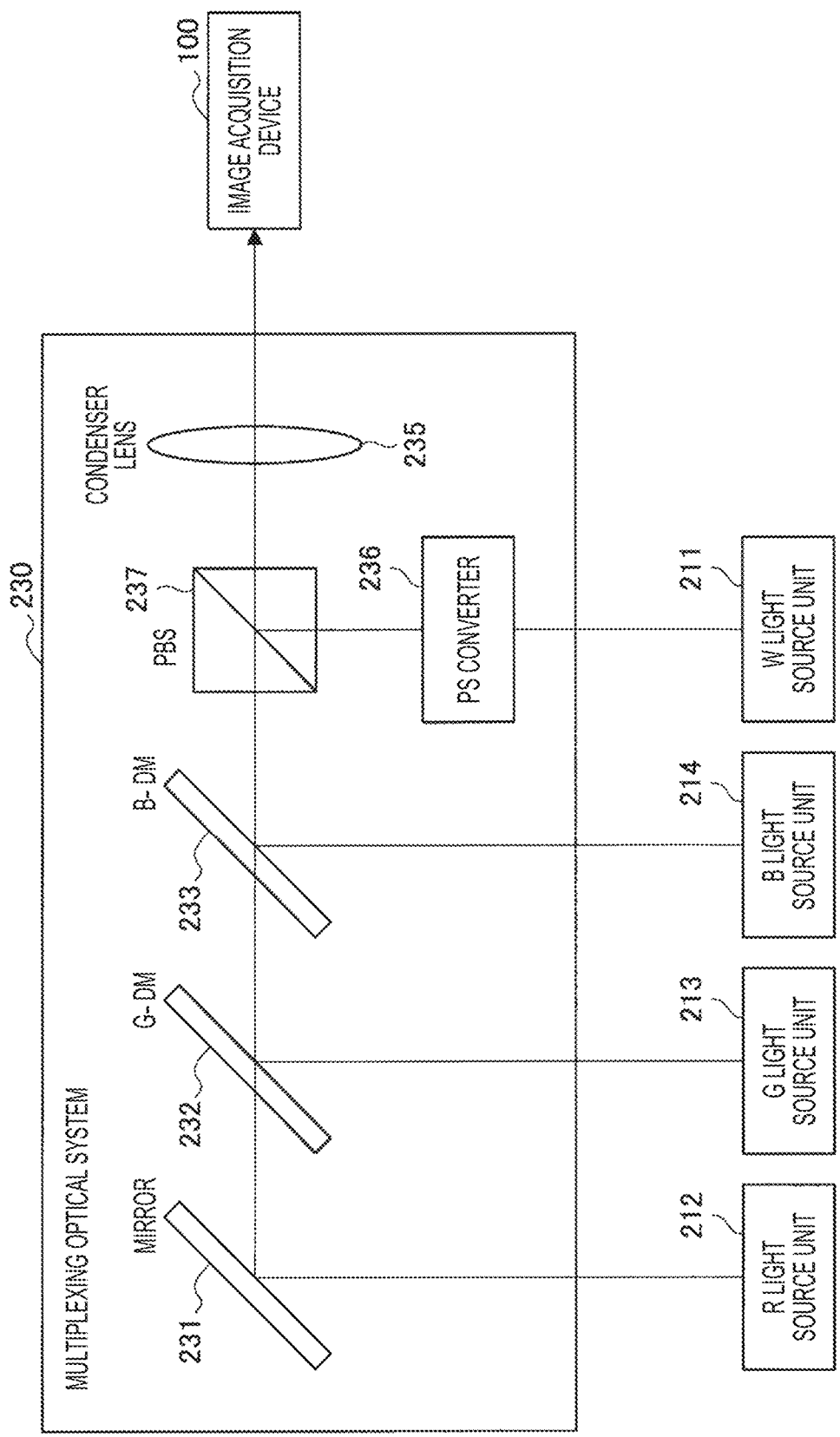
FIG. 4 is a block diagram illustrating an example of the configuration of the multiplexing optical system according to the present embodiment.

The multiplexing optical system 230 functions as a generation unit that multiplexes multiple types of light emitted from the each-color light source units 210 to generate white light. Note that, a configuration and multiplexing method of the multiplexing optical system 230 are arbitrary. Here, with reference to FIGS. 3 and 4, an example will be described of the configuration of the multiplexing optical system 230 according to the present embodiment. FIGS. 3 and 4 are block diagrams each illustrating an example of the configuration of the multiplexing optical system 230 according to the present embodiment.

As illustrated in FIG. 3, the multiplexing optical system 230 according to the present embodiment includes, for example, a mirror 231, three types of dichroic mirrors (indicated as "G-DM 232", "B-DM 233", and "W-DM 234" in FIG. 3), and a condenser lens 235.

The red light emitted from the R light source unit 212 changes its optical path due to the mirror 231, passes through the three types of dichroic mirrors (G-DM 232, B-DM 233, W-DM 234), and is incident on the condenser lens 235. The green light emitted from the G light source unit 213 changes its optical path due to the G-DM 232 having a characteristic of transmitting light of a wavelength longer than that of the red light and reflecting the green light, to be multiplexed with the red light, and passes through the two types of dichroic mirrors (B-DM 233, W-DM 234) and is incident on the condenser lens 235. The blue light emitted from the B light source unit 214 changes its optical path due to the B-DM 233 having a characteristic of transmitting light of a wavelength longer than that of the green light and reflecting the blue light, to be multiplexed with the red light and the green light, and passes through the W-DM 234 and is incident on the condenser lens 235.

The white light emitted from the W light source unit 211 changes its optical path due to the W-DM 234 having a characteristic of transmitting the red light, the green light, and the blue light and reflecting light of the rest of the wavelength band, to be multiplexed with the red light, the green light, and the blue light, and is incident on the condenser lens 235. The multiplexed light condensed by the condenser lens 235 is incident on the image acquisition device 100. Note that, the configuration illustrated in FIG. 3 is merely an example, and may be changed as appropriate. For example, a collimating lens or the like may be provided that generates parallel light by transmitting light, or a rod integrator or the like may be provided in the subsequent stage of the condenser lens 235 to equalize the in-plane intensity of the multiple types of color light.

Furthermore, polarization multiplexing may be performed by using the fact that the polarization directions are preserved of the respective multiple types of color light (laser light) emitted from the R light source unit 212, the G light source unit 213, and the B light source unit 214. More specifically, as illustrated in FIG. 4, the light source unit 200 may include a PS converter 236 and a polarizing beam splitter (PBS) 237 instead of the W-DM 234, and the white light emitted from the W light source unit 211 may be incident on the PBS 237 in a state where the polarization direction is aligned by the PS converter 236, and multiplexed with the narrow band light such that the polarization planes are orthogonal to each other, by the PBS 237. Note that, the configuration illustrated in FIG. 4 is merely an example, and may be changed as appropriate. For example, a member other than the PS converter 236 may be used if the polarization direction can be selectively controlled, or a member other than the PBS 237 may be used if polarization multiplexing is possible.

(Image Acquisition Device 100)

Figure 5:
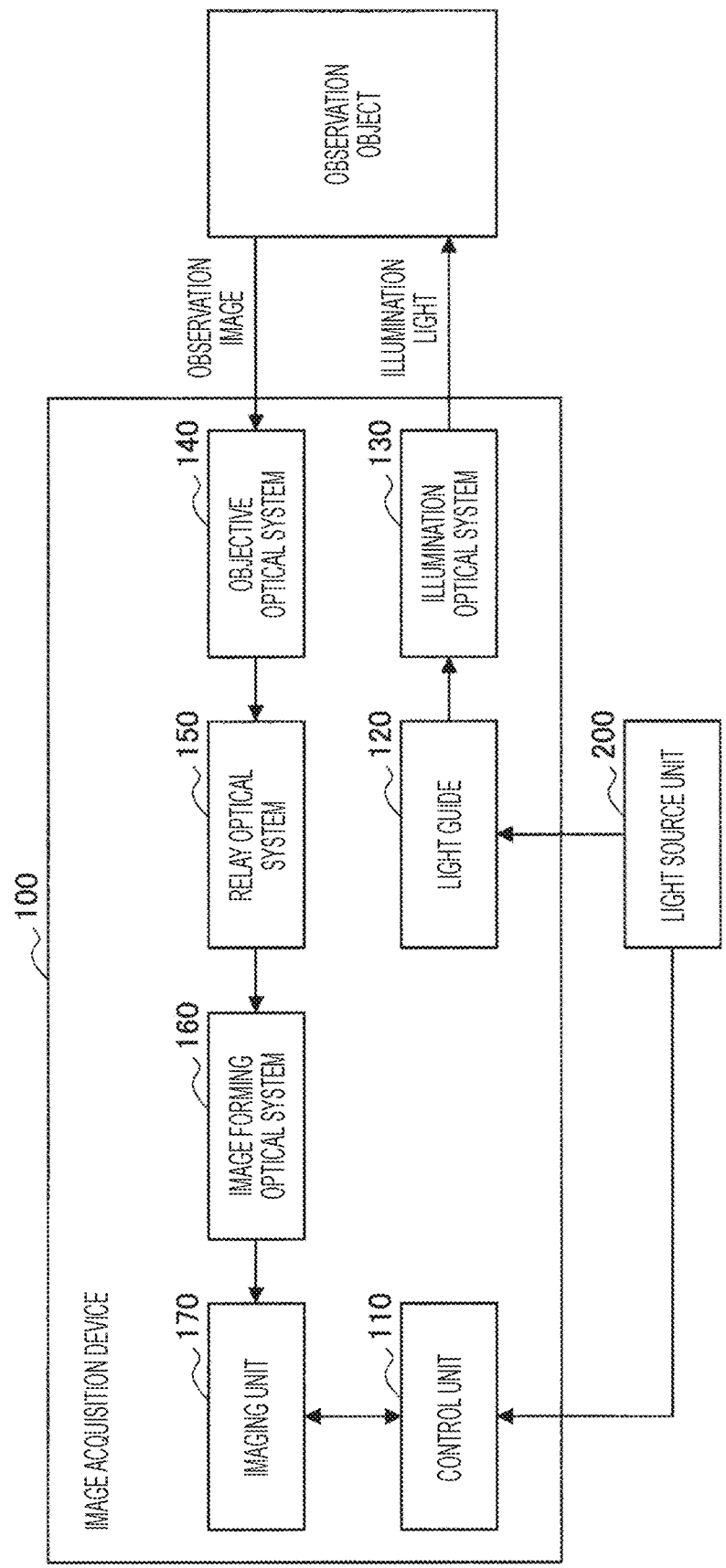
FIG. 5 is a block diagram illustrating an example of a configuration of an image acquisition device according to the present embodiment.

Subsequently, with reference to FIG. 5, a configuration will be described of the image acquisition device 100 according to the present embodiment. FIG. 5 is a block diagram illustrating an example of the configuration of the image acquisition device 100 according to the present embodiment. As illustrated in FIG. 5, the image acquisition device 100 according to the present embodiment includes the control unit 110, a light guide 120, an illumination optical system 130, an objective optical system 140, a relay optical system 150, an image forming optical system 160, and an imaging unit 170.

(Light Guide 120)

The light guide 120 is usually a bundled plurality of multimode optical fibers of an index guide type having a core diameter of about 10 [μm] to 80 [μm]. The light guide 120 is connected to the light source unit 200, and guides the multiplexed light input by the light source unit 200 to the illumination optical system 130. The light guide 120 is not particularly limited, and any of various known light guides can be used.

(Illumination Optical System 130)

The illumination optical system 130 is an optical system that adjusts an image forming state of the illumination light propagated by the light guide 120 on an observation object. The illumination optical system 130 is not particularly limited, and any of various known illumination optical systems can be used.

(Objective Optical System 140)

The objective optical system 140 is an optical system for obtaining an observation image of the irradiation area of the illumination light. The objective optical system 140 is not particularly limited, and any of various known optical systems can be used. The observation image propagated by the objective optical system 140 is further guided by the relay optical system 150 to the image forming optical system 160.

(Relay Optical System 150)

The relay optical system 150 is an optical system that relays the image observed by the objective optical system 140 to the image forming optical system 160. Note that, the relay optical system 150 is not particularly limited, and any of various known relay optical systems can be used.

(Image Forming Optical System 160)

The image forming optical system 160 is an optical system for forming an image of the observation image of the observation object propagated by the relay optical system 150 on the imaging unit 170, and is optically connected to the imaging unit 170 in the subsequent stage. The image forming optical system 160 is not particularly limited, and any of various known image forming optical systems can be used.

(Imaging Unit 170)

The imaging unit 170 is configured to capture an observation image of the inside of a living body by the illumination light from the light source unit 200 under the control of the control unit 110 and generate image data of the captured image. More specifically, the imaging unit 170 captures an image close to a situation to be directly observed by the human eye by using an imaging element (for example, a CCD, a CMOS, or the like) sensitive to the wavelength of the visible light band, appropriately develops such an image, and then provides the image as an observation image to a display unit (not illustrated. A display, or the like), thereby allowing the observer to confirm the observation image through the display unit.

(Control Unit 110)

The control unit 110 is implemented by, for example, a central processing unit (CPU), a read only memory (ROM), a random access memory (RAM), and the like. The control unit 110 is configured to integrally control the entire function of the image acquisition system, and is, for example, a unit corresponding to a camera control unit (CCU) of the image acquisition system.

Furthermore, as described above, the control unit 110 according to the present embodiment functions as a prediction unit that predicts, by a predetermined method, the temperature of the area irradiated with the multiplexed light as the illumination light, and controls the outputs of the narrow band light and the wide band light on the basis of the prediction.

Here, as described above, the prediction method is arbitrary. For example, the control unit 110 may predict the temperature of the irradiation area on the basis of the amount of light of the reflected light or the scattered light, which is incident on the imaging element, from the irradiation area. More specifically, since the amount of light such as the reflected light incident on the imaging element has a correlation with the temperature of the irradiation area, the control unit 110 can predict the temperature of the irradiation area on the basis of the amount of light incident on the imaging element. For example, the control unit 110 may hold a table recording a correspondence between the amount of light incident on the imaging element and the temperature of the irradiation area, and predict the temperature of the irradiation area on the basis of the amount of light incident on the imaging element, and the table.

Furthermore, the amount of light incident on the imaging element also changes depending on a separation distance between the emission port of the illumination optical system 130 and the irradiation area, and the amount of the illumination light. Here, since the amount of light of the illumination light is known (specified by control information of the each-color light source unit 210 of the light source unit 200), the control unit 110 can predict the separation distance between the emission port and the irradiation area on the basis of the amount of light incident on the imaging element. Then, the control unit 110 may predict the temperature of the irradiation area on the basis of the separation distance. For example, the control unit 110 may hold a table recording a correspondence between the amount of light of the illumination light, the separation distance between the emission port and the irradiation area, and the temperature of the irradiation area, and predict the temperature of the irradiation area on the basis of the amount of the illumination light (known), the prediction result of the separation distance between the emission port and the irradiation area, and the table.

Note that, the control unit 110 may additionally consider duration of irradiation of the illumination light. More specifically, severity of the thermal damage may differ depending on the duration of irradiation of the illumination light. For example, even in a case where the amount of light of the illumination light is small, the thermal damage may occur or the thermal damage may become severe by continuous irradiation for a longer time. Thus, the control unit 110 can more appropriately prevent the occurrence of the thermal damage by, for example, adding information regarding the duration of irradiation of the illumination light to the above table.

Furthermore, the control unit 110 may determine the state of the irradiation area by analyzing the captured image, and predict the temperature of the irradiation area on the basis of the determination result. More specifically, the irradiation area may change visually along with the temperature rise in the irradiation area. For example, in a case where the inside of a living body is irradiated with the illumination light, protein may be denatured along with the temperature rise of the irradiation area, and the irradiation area may turn white. As the denaturation further progresses, carbonization of the protein may occur and the irradiation area may turn black. The control unit 110 may detect a change (for example, denaturation of protein or the like) accompanying the temperature rise in the irradiation area by analyzing the captured image, and predict the temperature of the irradiation area on the basis of the detection result.

Furthermore, the control unit 110 may predict the temperature of the irradiation area by using a device (for example, thermography or the like) that measures and visualizes heat of the irradiation area. For example, the image acquisition system according to the present embodiment may include thermography that images the irradiation area and measures the temperature of the irradiation area, and the control unit 110 may predict (or grasp) the temperature of the irradiation area on the basis of the output by the thermography device.

Note that, the temperature of the irradiation area predicted by the control unit 110 is not particularly limited, and may be the maximum value of the temperature in the irradiation area, or may be the average value of the temperatures in the irradiation area, or may be the temperature of a predetermined one point in the irradiation area.

Then, on the basis of the prediction of the temperature of the irradiation area, the control unit 110 controls the outputs of the narrow band light and the wide band light so that the output (brightness) and the color of the illumination light are not changed (or the amount of change in each of the output (brightness) and the color of the illumination light is maintained at a value within a predetermined range).

More specifically, regarding maintaining of the output (brightness), in a case where the predicted temperature of the irradiation area is higher than a predetermined threshold value and the risk of the thermal damage or burn injury is high, the control unit 110 performs control to decrease the amount of light of the wide band light. Then, the control unit 110 can make the total value of the amounts of light of the emitted multiple types of illumination light constant by increasing the amount of light of the narrow band light by the amount of light of the decreased wide band light. Note that, before and after the above control, the control unit 110 may change as appropriate the total value of the amounts of light of the multiple types of illumination light to the extent that does not interfere with the observation even if the total value is not constant.

Furthermore, more specifically, regarding maintaining of the color, the color is represented by a color temperature, and the color temperature of the illumination light is basically determined by the ratios at which the multiple types of color light are mixed. As described above, the control unit 110 performs control so that the color temperature of the illumination light becomes constant by adjusting the ratios at which the multiple types of color light are mixed, while keeping the total value of the amounts of light of the multiple types of illumination light constant before and after the control.

For example, it is assumed that, by simulation or the like in advance, a table is created recording a correspondence between the drive current (or drive voltage) of the each-color light source unit 210 and the amount of light to be emitted, and a correspondence between the drive current (or drive voltage) of the each-color light source unit 210 and the color temperature of the irradiation light. As a result, the control unit 110 can freely adjust the amount of light and the color temperature by increasing or decreasing the drive current of the each-color light source unit 210 by referring to the table. Upon determining the drive current of the each-color light source unit 210, the control unit 110 implements the above control by generating a control signal including the information and providing the signal to the each-color light source control unit 220. Note that, this method is merely an example, and may be changed as appropriate. Furthermore, before and after the above control, it is assumed that the imaging unit 170 does not change the gain of the imaging element (or holds the gain at a value within a predetermined range from a value before the change).

Note that, the above processing is merely an example, and the control unit 110 may perform various types of other processing. For example, the control unit 110 may perform processing of notifying the observer of various types of information (information regarding the risk of the thermal damage, information regarding the progress of the above processing content, and the like). For example, in a case where it is determined that the risk of the thermal damage is high, the control unit 110 may sound an alarm by controlling a sounding device (not illustrated. A speaker, or the like), or may display the information by controlling a display unit (not illustrated. A display or the like).

(2-3. Operation of Image Acquisition System According to the Present Embodiment)

Figure 6:
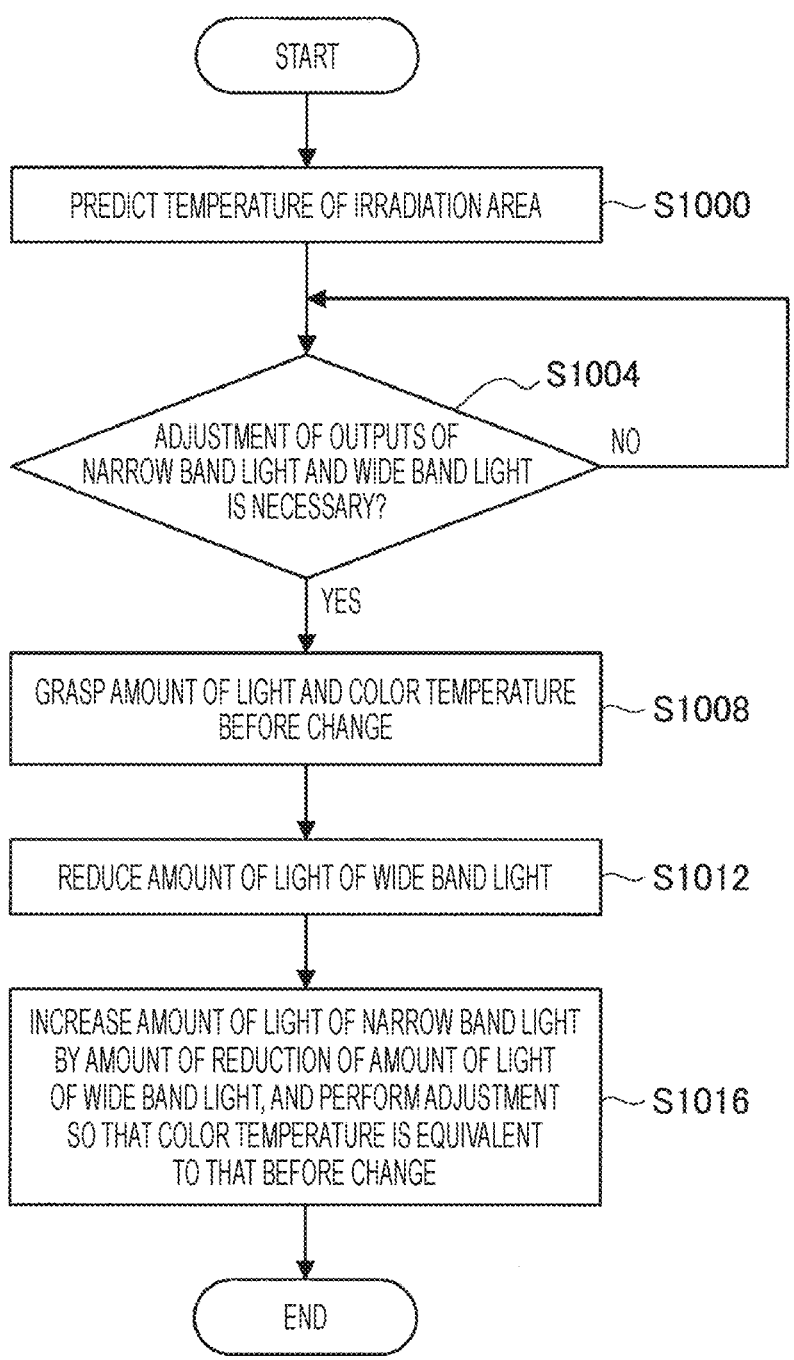
FIG. 6 is a flowchart illustrating an example of operation of an image acquisition system according to the present embodiment.

The configuration of the image acquisition system according to the present embodiment has been described above. Subsequently, with reference to FIG. 6, operation will be described of the image acquisition system according to the present embodiment. FIG. 6 is a flowchart illustrating an example of the operation of the image acquisition system according to the present embodiment.

In step S1000, the control unit 110 of the image acquisition device 100 predicts the temperature of the irradiation area of the illumination light on the basis of the amount of light incident on the imaging element, as described above, for example. As a result of the temperature prediction of the irradiation area, in a case where the control unit 110 determines that adjustment of the outputs of the narrow band light and the wide band light is necessary (for example, a case where the temperature of the irradiation area is higher than a predetermined threshold value, a case where the temperature of the irradiation area is increased at a faster pace than a predetermined threshold value, or the like) (step S1004/Yes), in step S1008, the control unit 110 grasps the amounts of light before the change (the amount of light of the light emitted from the each-color light source control unit 220, the amount of light of the illumination light, and the like), and the color temperatures (the color temperature of the light emitted from the each-color light source control unit 220, the color temperature of the illumination light, and the like).

Here, a grasping method is arbitrary. For example, the control unit 110 may confirm the drive current of the each-color light source control unit 220, and calculate the amount of light and the color temperature on the basis of the drive current. Note that, as a result of the temperature prediction of the irradiation area, in a case where the control unit 110 determines that the adjustment of the outputs of the narrow band light and the wide band light is unnecessary (step S1004/No), the processing after step S1008 is not performed.

In step S1012, the control unit 110 reduces the amount of light of the white light that is the wide band light. Here, the amount of reduction of the amount of light of the white light is arbitrary. For example, the control unit 110 may determine the amount of reduction of the amount of light of the white light depending on the temperature of the irradiation area or the temperature rise speed. In step S1016, the control unit 110 increases the amount of light of the narrow band light by the amount of reduction of the amount of light of the white light. In other words, the control unit 110 increases the total value of the amounts of light of the multiple types of color light (red light, green light, blue light) each being the narrow band light by the amount of reduction of the amount of light of the white light. As a result, the control unit 110 can maintain the output (brightness) of the illumination light constant by maintaining the total value of the amounts of light of the multiple types of illumination light constant. The control unit 110 additionally adjusts the ratios at which the multiple types of color light are mixed so that the color temperature of the illumination light after the change is equivalent to the color temperature of the illumination light before the change.

By the above operation, the control unit 110 according to the present embodiment can reduce the temperature of the irradiation area while causing the output (brightness) and the color of the illumination light to be kept from changing (or causing the amount of change in each of the output (brightness) and the color of the illumination light to be maintained at a value within a predetermined range). Furthermore, the control unit 110 according to the present embodiment can continue causing the light source unit 200 to continuously emit more appropriate illumination light by continuously repeating the operation illustrated in FIG. 6.

3. Image Acquisition System According to Modification

The operation of the image acquisition system according to the present embodiment has been described above. Subsequently, an image acquisition system according to a modification of the present disclosure will be described.

In the above embodiment, the control unit 110 grasps the amount of light and the color temperature before the change, and changes the drive current of the each-color light source control unit 220 so that the values of the amount of light and the color temperature become constant (or differences from the values before the change are maintained in predetermined ranges), as illustrated in FIG. 6, for example. On the other hand, the image acquisition system according to the modification of the present disclosure includes a color sensor capable of sensing multiplexed light, and the control unit 110 controls the drive current of the each-color light source control unit 220 on the basis of an output from the color sensor.

It is assumed that, when the multiplexed light is input, the color sensor outputs a component corresponding to red light as an R signal, outputs a component corresponding to green light as a G signal, and outputs a component corresponding to blue light as a B signal. In this modification, the control unit 110 can cause the output (brightness) and the color of the illumination light to be constant before and after the change by a simpler method that causes the value of each signal (R signal, G signal, B signal) that is the output of the color sensor to be constant before and after the change (or causes the difference to be maintained within a predetermined range).

Figure 7:
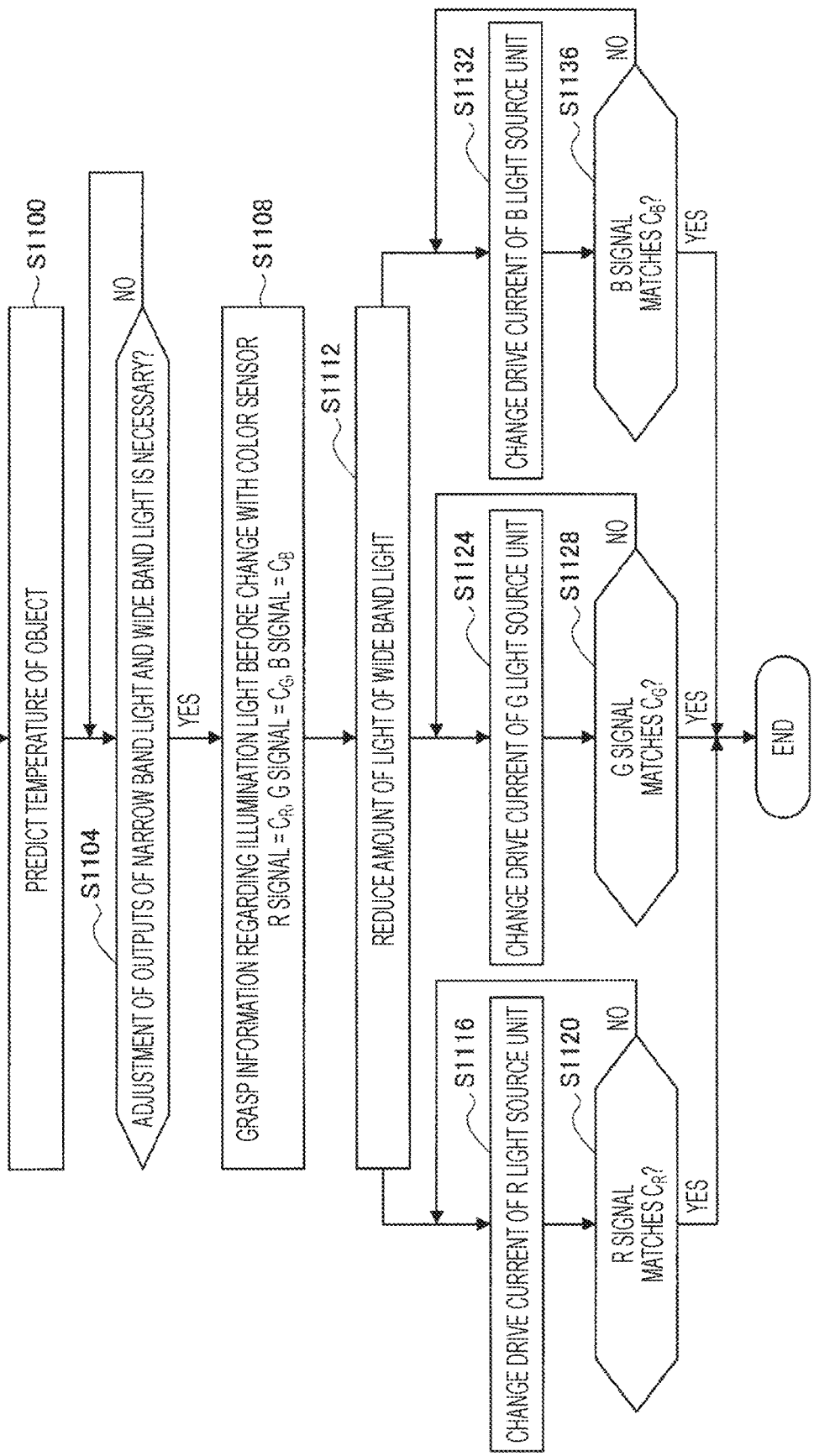
FIG. 7 is a flowchart illustrating an example of operation of an image acquisition system according to a modification.

Here, with reference to FIG. 7, operation will be described of the image acquisition system according to the modification. FIG. 7 is a flowchart illustrating an example of the operation of the image acquisition system according to the modification.

In step S1100, the control unit 110 of the image acquisition device 100 predicts the temperature of the irradiation area of the illumination light on the basis of the amount of light incident on the imaging element, as described above, for example. As a result of the temperature prediction of the irradiation area, in a case where the control unit 110 determines that adjustment of the outputs of the narrow band light and the wide band light is necessary (for example, a case where the predicted temperature is higher than a predetermined threshold value, a case where the predicted temperature is increased at a faster pace than a predetermined threshold value, or the like) (step S1104/Yes), in step S1108, the control unit 110 grasps information regarding the illumination light before the change on the basis of the signal output from the color sensor. Here, the value of the R signal output from the color sensor before the change is set as $C_R$, the value of the G signal is set as $C_G$, and the value of the B signal is set as $C_B$.

In step S1112, the control unit 110 reduces the amount of light of the white light that is the wide band light. In step S1116, the control unit 110 changes the drive current of the R light source unit 212, and confirms whether or not the value of the R signal output from the color sensor matches $C_R$ that is the value before the change, and in a case where the value of the R signal does not match $C_R$ (step S1120/No), the drive current of the R light source unit 212 is changed again in step S1116. In a case where the value of the R signal matches $C_R$ (step S1120/Yes), the processing for the R light source unit 212 ends.

In step S1124, the control unit 110 changes the drive current of the G light source unit 213, and confirms whether or not the value of the G signal output from the color sensor matches $C_G$ that is the value before the change, and in a case where the value of the G signal does not match $C_G$ (step S1128/No), the drive current of the G light source unit 213 is changed again in step S1124. In a case where the value of the G signal matches $C_G$ (step S1128/Yes), the processing for the G light source unit 213 ends.

In step S1132, the control unit 110 changes the drive current of the B light source unit 214, and confirms whether or not the value of the B signal output from the color sensor matches $C_B$ that is the value before the change, and in a case where the value of the B signal does not match $C_B$ (step S1136/No), the drive current of the B light source unit 214 is changed again in step S1132. In a case where the value of the B signal matches $C_B$ (step S1136/Yes), the processing for the B light source unit 214 ends.

By the above operation, the control unit 110 according to the modification can reduce the temperature of the irradiation area while causing the output (brightness) and the color of the illumination light to be constant (or causing the differences to be maintained within predetermined ranges) before and after the change by a simpler method using the color sensor.

4. Hardware Configuration

Figure 8:
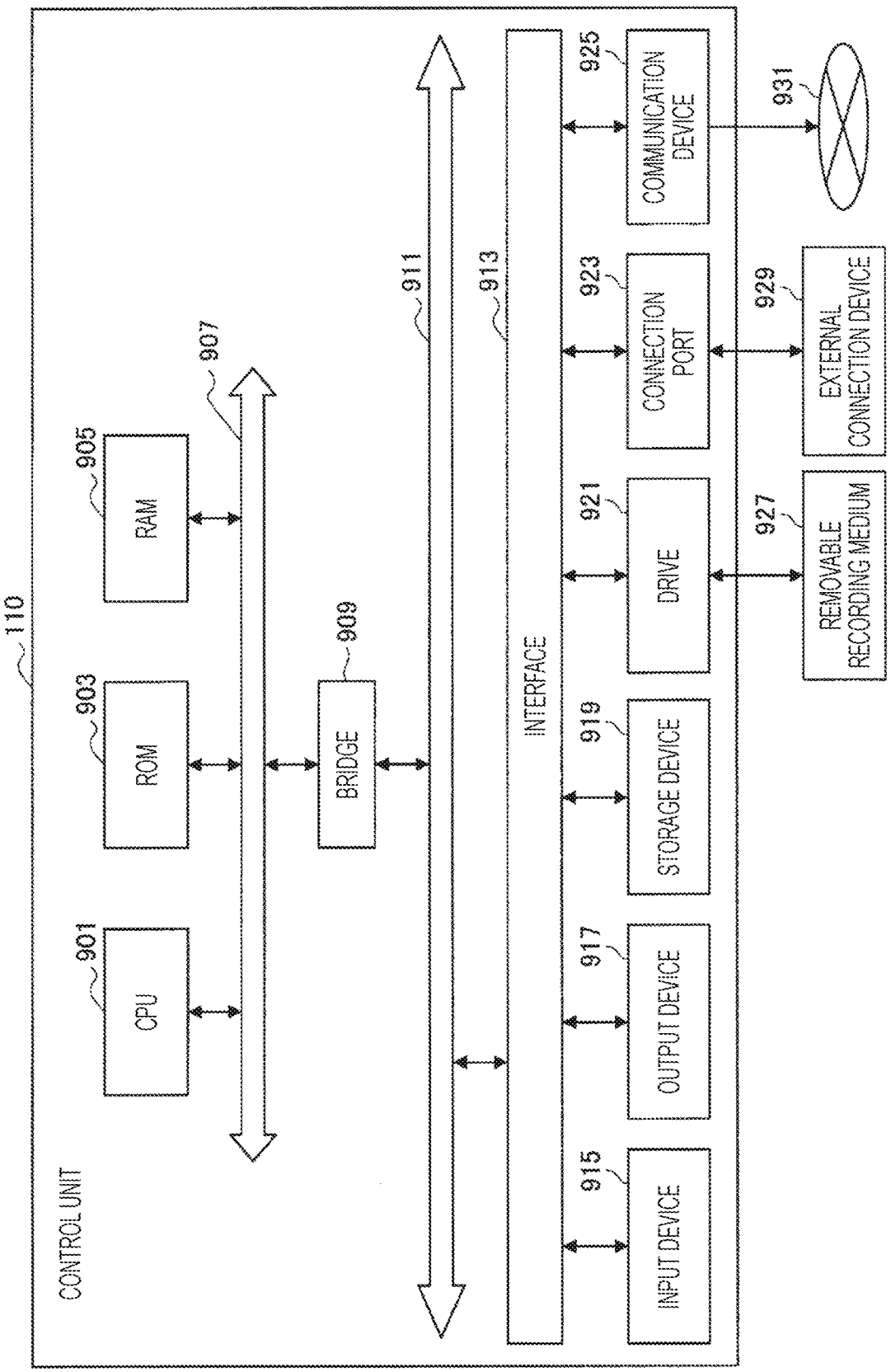
FIG. 8 is a block diagram illustrating an example of a hardware configuration of a control unit according to the present disclosure.

Next, with reference to FIG. 8, a hardware configuration will be described in detail of the control unit 110 according to the present disclosure. FIG. 8 is a block diagram illustrating an example of the hardware configuration of the control unit 110 according to the present disclosure.

The control unit 110 mainly includes a CPU 901, ROM 903, and RAM 905. Furthermore, the control unit 110 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls overall operation or a part thereof in the control unit 110 or in the image acquisition device 100 in accordance with various programs recorded in the ROM 903, the RAM 905, the storage device 919, or a removable recording medium 927. The ROM 903 stores programs to be used by the CPU 901, calculation parameters, and the like. The RAM 905 temporarily stores programs to be used by the CPU 901, parameters that change as appropriate in the execution of the programs, and the like. These are connected to each other by the host bus 907 including an internal bus such as a CPU bus.

The host bus 907 is connected to the external bus 911 such as a peripheral component interconnect/interface (PCI) bus via the bridge 909.

The input device 915 is an operation means operated by a user, for example, a mouse, a keyboard, a touch panel, a button, a switch, a lever, or the like. Furthermore, the input device 915 may be, for example, a remote control means (so-called remote controller) using infrared rays or other radio waves, or an external connection device 929 such as a mobile phone or a PDA adaptable to the operation of the control unit 110. Moreover, the input device 915 includes, for example, an input control circuit that generates an input signal on the basis of information input by the user using the above operation means and outputs the signal to the CPU 901, and the like. By operating the input device 915, the user can input various data to the control unit 110 and give an instruction to perform processing operation.

The output device 917 includes a device that can visually or aurally notify the user of acquired information. Examples of the device include: a display device such as a CRT display device, a liquid crystal display device, a plasma display device, an EL display device, or a lamp; an audio output device such as a speaker or a headphone; a printer device; a mobile phone; a facsimile; and the like. The output device 917 outputs, for example, a result obtained by various types of processing performed by the control unit 110. Specifically, the display device displays the result obtained by the various types of processing performed by the control unit 110 as a text or an image. On the other hand, the audio output device converts an audio signal including reproduced audio data, acoustic data, and the like into an analog signal to output the signal.

The storage device 919 is a device for storing data configured as an example of a storage unit of the control unit 110. The storage device 919 includes, for example, a magnetic storage device such as a hard disk drive (HDD), a semiconductor storage device, an optical storage device, a magneto-optical storage device, or the like. The storage device 919 stores various data and programs executed by the CPU 901, various data acquired from the outside, and the like.

The drive 921 is a reader/writer for a recording medium, and is incorporated in the control unit 110 or externally attached thereto. The drive 921 reads information recorded on the removable recording medium 927 such as a mounted magnetic disk, optical disk, magneto-optical disk, or semiconductor memory, and outputs the information to the RAM 905. Furthermore, the drive 921 can also write a record onto the removable recording medium 927 such as a mounted magnetic disk, optical disk, magneto-optical disk, or semiconductor memory.

The removable recording medium 927 is, for example, a DVD medium, an HD-DVD medium, a Blu-ray (registered trademark) medium, or the like. Furthermore, the removable recording medium 927 may be a CompactFlash (registered trademark) (CF), a flash memory, a secure digital memory card (SD memory card), or the like. Furthermore, the removable recording medium 927 may be, for example, an integrated circuit card (IC card) mounting a non-contact type IC chip, an electronic device, or the like.

The connection port 923 is a port for directly connecting a device to the control unit 110. As an example of the connection port 923, there are a universal serial bus (USB) port, an IEEE 1394 port, a small computer system interface (SCSI) port, and the like. As another example of the connection port 923, there are an RS-232C port, an optical audio terminal, a high-definition multimedia interface (HDMI) (registered trademark) port, and the like. By connecting the external connection device 929 to the connection port 923, the control unit 110 directly acquires various data from the external connection device 929, or provides various data to the external connection device 929.

The communication device 925 is, for example, a communication interface including a communication device or the like for connecting to the communications network 931. The communication device 925 is, for example, a communication card for a wired or wireless local area network (LAN), Bluetooth (registered trademark), Wireless USB (WUSB), or the like. Furthermore, the communication device 925 may be a router for optical communication, a router for an asymmetric digital subscriber line (ADSL), a modem for various types of communication, or the like. For example, the communication device 925 can transmit and receive signals and the like according to a predetermined protocol, for example, TCP/IP or the like, with the Internet or another communication device. Furthermore, the communications network 931 connected to the communication device 925 includes a network or the like connected by wire or wirelessly, and may be, for example, the Internet, a home LAN, infrared communication, radio wave communication, satellite communication, or the like.

In the above, an example has been illustrated of the hardware configuration that can implement the function of the control unit 110 according to the present disclosure. Each of the components described above may be configured using a general-purpose member, or may be configured by hardware specialized for the function of each component. It is therefore possible to change the hardware configuration to be used as appropriate depending on the technical level of each implementation of the above embodiment or modification.

5. Conclusion

As described above, the image acquisition system, the image acquisition method, the control device, and the control method according to the present disclosure are able to prevent the occurrence of the thermal damage by predicting the temperature of the area irradiated with the illumination light generated by the narrow band light and the wide band light, and controlling the outputs of the narrow band light and the wide band light on the basis of the prediction. Furthermore, the image acquisition system, the image acquisition method, the control device, and the control method according to the present disclosure are able to cause the output (brightness) and the color of the illumination light to be constant before and after the above control. Furthermore, the image acquisition system, the image acquisition method, the control device, and the control method according to the modification are able to cause the output (brightness) and the color of the illumination light to be constant before and after the control by the simpler method using the color sensor.

In the above, the preferred embodiments of the present disclosure have been described in detail with reference to the accompanying drawings; however, the technical scope of the present disclosure is not limited to such examples. It is obvious that persons having ordinary knowledge in the technical field of the present disclosure can conceive various modification examples or correction examples within the scope of the technical idea described in the claims, and it is understood that the modification examples or correction examples also belong to the technical scope of the present disclosure.

For example, the steps illustrated in the above flowcharts do not necessarily have to be processed in chronological order according to the order described as the flowcharts. In other words, the steps may be processed in an order different from the order described as the flowchart, or may be processed in parallel.

Furthermore, the functional configuration of the image acquisition device 100 or the light source unit 200 may be changed as appropriate. For example, a part of the functional configuration of the image acquisition device 100 or the light source unit 200 may be included in an external device as appropriate. Furthermore, some of the functions of the image acquisition device 100 may be embodied by the control unit 110. Furthermore, some of the functions of the light source unit 200 may be embodied by the each-color light source control unit 220, or the control unit 110 of the image acquisition device 100.

Furthermore, in a case where it is determined that the thermal damage cannot be prevented only by controlling the outputs of the narrow band light and the wide band light, the image acquisition system according to the present disclosure may perform processing of reducing the amount of light of the illumination light and increasing the gain of the imaging element. For example, in a case where the emission port of the illumination light comes too close to an irradiation target due to an erroneous operation or the like, it may be difficult to prevent the thermal damage only by controlling the outputs of the narrow band light and the wide band light. At that time, the image acquisition system according to the present disclosure may prevent the thermal damage by performing the processing of reducing the amount of light of the illumination light and increasing the gain of the imaging element (or switching to a mode in which the processing is performed).

Furthermore, some of the various types of processing described above may be performed manually by the observer. For example, the processing of reducing the output of the wide band light and increasing the output of the narrow band light may be performed by the observer. At that time, the image acquisition system according to the present disclosure may perform auxiliary processing such as providing various types of information (information regarding the amount of light, information regarding the color temperature, information regarding the temperature of the irradiation area, and the like) so that the observer can work more appropriately.

Furthermore, the effects described in the present specification are merely illustrative or exemplary and not restrictive. That is, the technology according to the present disclosure can exhibit other effects obvious to those skilled in the art from the description of the present specification together with the above-described effects or in place of the above-described effects.

Note that, the following configurations also belong to the technical scope of the present disclosure.

(1)

An image acquisition system including:

a first light source unit that emits narrow band light having a peak intensity in a specific band;

a second light source unit that emits wide band light having a band wider than the specific band;

a generation unit that generates multiplexed light by using the narrow band light and the wide band light;

an imaging unit that images an irradiation target of the multiplexed light;

a prediction unit that performs prediction of a temperature of an area irradiated with the multiplexed light in the irradiation target; and a control unit that performs control of outputs of the narrow band light and the wide band light on the basis of the prediction.

(2)

The image acquisition system according to (1), in which in a case where the temperature is predicted to be higher than a predetermined value, the control unit decreases the output of the wide band light and increases the output of the narrow band light.

(3)

The image acquisition system according to (1) or (2), in which in a case where the temperature is predicted to be lower than a predetermined value, the control unit increases the output of the wide band light and decreases the output of the narrow band light.

(4)

The image acquisition system according to any one of (1) to (3), in which the control unit performs the control such that an amount of light of the multiplexed light is maintained at a constant value or a value within a predetermined range from the constant value, before and after the control.

(5)

The image acquisition system according to any one of (1) to (4), in which the control unit performs the control such that a color temperature of the multiplexed light is maintained at a constant value or a value within a predetermined range from the constant value, before and after the control.

(6)

The image acquisition system according to (4) or (5), in which the control unit performs the control on the basis of an output by a color sensor to which the multiplexed light is input.

(7)

The image acquisition system according to any one of (1) to (6), in which the imaging unit maintains a gain of an imaging element at a constant value or a value within a predetermined range from the constant value, before and after the control.

(8)

The image acquisition system according to any one of (1) to (7), in which the prediction unit performs the prediction on the basis of incidence of reflected light or scattered light from the irradiation target on the imaging unit.

(9)

The image acquisition system according to (8), in which the prediction unit predicts a separation distance between an emission port from which the multiplexed light is emitted and the irradiation target on the basis of the incidence, and performs the prediction on the basis of the separation distance.

(10)

The image acquisition system according to any one of (1) to (7), in which the prediction unit performs the prediction on the basis of an analysis of a captured image in which the irradiation target is imaged, or an output by thermography in which the irradiation target is imaged.

(11)

The image acquisition system according to any one of (1) to (10), in which the generation unit generates the multiplexed light that is white light.

(12)

The image acquisition system according to (11), in which the first light source unit emits a plurality of types of the narrow band light that generates white light by being multiplexed with each other.

(13)

The image acquisition system according to (11) or (12), in which the second light source unit emits white light as the wide band light.

(14)

The image acquisition system according to any one of (1) to (13), in which the image acquisition system is an endoscope system or a microscope system.

(15)

An image acquisition method executed by a computer, the image acquisition method including:

emitting narrow band light having a peak intensity in a specific band;

emitting wide band light having a band wider than the specific band;

generating multiplexed light by using the narrow band light and the wide band light;

imaging an irradiation target of the multiplexed light;

performing prediction of a temperature of an area irradiated with the multiplexed light in the irradiation target; and performing control of outputs of the narrow band light and the wide band light on the basis of the prediction.

(16)

A control device including:

a control unit that performs control of outputs of narrow band light and wide band light on the basis of prediction of a temperature of an irradiation area of multiplexed light generated by using the narrow band light having a peak intensity in a specific band and the wide band light having a band wider than the specific band.

(17)

A control method executed by a computer, the control method including:

performing control of outputs of narrow band light and wide band light on the basis of prediction of a temperature of an irradiation area of multiplexed light generated by using the narrow band light having a peak intensity in a specific band and the wide band light having a band wider than the specific band.

REFERENCE SIGNS LIST

100 Image acquisition device
110 Control unit
120 Light guide
130 Illumination optical system
140 Objective optical system
150 Relay optical system
160 Image forming optical system
170 Imaging unit
200 Light source unit
210 Each-color light source unit
220 Each-color light source control unit
230 Multiplexing optical system

The invention claimed is:

1. An image acquisition system comprising:
a first light source that emits narrow band light having a peak intensity in a specific band;
a second light source that emits wide band light having a band wider than the specific band;
a multiplexing optical system that generates multiplexed light by using the narrow band light and the wide band light;
an image sensor that images an irradiation target of the multiplexed light; and
processing circuitry configured to
perform prediction of a temperature of an area irradiated with the multiplexed light in the irradiation target, and
perform control of outputs of the narrow band light and the wide band light on a basis of the prediction, wherein
in a case where the temperature is predicted to be higher than a predetermined value, the processing circuitry decreases the output of the wide band light and increases the output of the narrow band light.

2. The image acquisition system according to claim 1, wherein
the processing circuitry performs the control such that an amount of light of the multiplexed light is maintained at a constant value or a value within a predetermined range from the constant value, before and after the control.

3. The image acquisition system according to claim 2, wherein
the processing circuitry performs the control on a basis of an output by a color sensor to which the multiplexed light is input.

4. The image acquisition system according to claim 1, wherein
the processing circuitry performs the control such that a color temperature of the multiplexed light is maintained at a constant value or a value within a predetermined range from the constant value, before and after the control.

5. The image acquisition system according to claim 1, wherein
the image sensor maintains a gain of an imaging element at a constant value or a value within a predetermined range from the constant value, before and after the control.

6. The image acquisition system according to claim 1, wherein the processing circuitry performs the prediction on a basis of incidence of reflected light or scattered light from the irradiation target on the image sensor.

7. The image acquisition system according to claim 6, wherein
the processing circuitry predicts a separation distance between an emission port from which the multiplexed light is emitted and the irradiation target on a basis of the incidence, and performs the prediction on a basis of the separation distance.

8. The image acquisition system according to claim 1, wherein
the processing circuitry performs the prediction on a basis of an analysis of a captured image in which the irradiation target is imaged, or an output by thermography in which the irradiation target is imaged.

9. The image acquisition system according to claim 1, wherein
the multiplexing optical system generates the multiplexed light that is white light.

10. The image acquisition system according to claim 9, wherein
the first light source emits a plurality of types of the narrow band light that generates white light by being multiplexed with each other.

11. The image acquisition system according to claim 9, wherein
the second light source emits white light as the wide band light.

12. The image acquisition system according to claim 1, wherein
the image acquisition system is an endoscope system or a microscope system.

13. An image acquisition system comprising:
a first light source that emits narrow band light having a peak intensity in a specific band;
a second light source that emits wide band light having a band wider than the specific band;
a multiplexing optical system that generates multiplexed light by using the narrow band light and the wide band light;
an image sensor that images an irradiation target of the multiplexed light and processing circuitry configured to
perform prediction of a temperature of an area irradiated with the multiplexed light in the irradiation target, and
perform control of outputs of the narrow band light and the wide band light on a basis of the prediction, wherein
in a case where the temperature is predicted to be lower than a predetermined value, the processing circuitry increases the output of the wide band light and decreases the output of the narrow band light.

14. The image acquisition system according to claim 13, wherein
the processing circuitry performs the control such that an amount of light of the multiplexed light is maintained at a constant value or a value within a predetermined range from the constant value, before and after the control.

15. The image acquisition system according to claim 14, wherein
the processing circuitry performs the control on a basis of an output by a color sensor to which the multiplexed light is input.

16. The image acquisition system according to claim 13, wherein
the processing circuitry performs the control such that a color temperature of the multiplexed light is maintained at a constant value or a value within a predetermined range from the constant value, before and after the control.

17. The image acquisition system according to claim 13, wherein
the image sensor maintains a gain of an imaging element at a constant value or a value within a predetermined range from the constant value, before and after the control.

18. The image acquisition system according to claim 13, wherein
the processing circuitry performs the prediction on a basis of incidence of reflected light or scattered light from the irradiation target on the image sensor.

19. The image acquisition system according to claim 18, wherein
the processing circuitry predicts a separation distance between an emission port from which the multiplexed light is emitted and the irradiation target on a basis of the incidence, and performs the prediction on a basis of the separation distance.

20. The image acquisition system according to claim 13, wherein
the processing circuitry performs the prediction on a basis of an analysis of a captured image in which the irradiation target is imaged, or an output by thermography in which the irradiation target is imaged.

* * * * *